United States Patent
Tessel et al.

(10) Patent No.: US 10,383,581 B2
(45) Date of Patent: Aug. 20, 2019

(54) CONTROLLING A VITAL SIGN DISPLAY DEVICE TO DETERMINE WHETHER A MOST RECENTLY RECEIVED FRAME OF A VITAL SIGN IMAGE STREAM IS BEING DISPLAYED

(71) Applicant: KONINKLIJKE PHILIPS N.V., Eindhoven (NL)

(72) Inventors: Uli Tessel, Ehningen (DE); Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 71 days.

(21) Appl. No.: 15/668,730

(22) Filed: Aug. 4, 2017

(65) Prior Publication Data
US 2017/0325753 A1    Nov. 16, 2017

Related U.S. Application Data

(63) Continuation of application No. 14/240,055, filed as application No. PCT/IB2012/054434 on Aug. 29, 2012, now abandoned.

(60) Provisional application No. 61/531,683, filed on Sep. 7, 2011.

(51) Int. Cl.
| | | |
|---|---|---|
| *A61B 5/00* | (2006.01) | |
| *G06T 1/00* | (2006.01) | |
| *G09G 5/377* | (2006.01) | |
| *G06T 7/231* | (2017.01) | |
| *G06K 9/00* | (2006.01) | |
| *G06T 7/285* | (2017.01) | |

(52) U.S. Cl.
CPC .......... *A61B 5/7425* (2013.01); *G06K 9/0051* (2013.01); *G06T 1/00* (2013.01); *G06T 1/0021* (2013.01); *G06T 7/231* (2017.01); *G09G 5/377* (2013.01); *G06T 7/285* (2017.01); *G06T 2207/20068* (2013.01)

(58) Field of Classification Search
None
See application file for complete search history.

(56) References Cited

U.S. PATENT DOCUMENTS

| | | |
|---|---|---|
| 5,947,572 A | 9/1999 | Chang |
| 6,216,228 B1 | 4/2001 | Chapman |
| 2003/0185417 A1 | 10/2003 | Alattar |
| 2006/0115108 A1 | 6/2006 | Rodriguez |
| 2006/0233420 A1 | 10/2006 | Rhoads |

(Continued)

FOREIGN PATENT DOCUMENTS

| | | |
|---|---|---|
| EP | 1814307 | 8/2007 |
| JP | 2010258645 | 11/2010 |
| WO | 03062960 | 7/2003 |

OTHER PUBLICATIONS

Lin, et al., "A review of data hiding images", PICS. 1999.

*Primary Examiner* — Vu Nguyen

(57) ABSTRACT

The display of correct and reliable operating image data which may change over the time is correctly and reliably displayed. A secured image is generated based on a source image by generating at least one secured image part. The secured image part is generated by combining a source image part of the source image with a corresponding secure pattern. The displaying of the secured image is monitored by detecting the corresponding secure pattern of the secured image part, updating the detected secure pattern, checking the currentness or correctness of the detected secure pattern.

11 Claims, 9 Drawing Sheets

(56) References Cited

U.S. PATENT DOCUMENTS

| | | |
|---|---|---|
| 2006/0236200 A1 | 10/2006 | Tanaka |
| 2007/0063998 A1 | 3/2007 | Mahesh |
| 2009/0150292 A1 | 6/2009 | Trinh |
| 2010/0169642 A1 | 7/2010 | Wise |

CONTROLLING A VITAL SIGN DISPLAY DEVICE TO DETERMINE WHETHER A MOST RECENTLY RECEIVED FRAME OF A VITAL SIGN IMAGE STREAM IS BEING DISPLAYED

CROSS REFERENCE TO RELATED APPLICATIONS

This application is a continuation/divisional of U.S. application Ser. No. 14/240,055, filed Feb. 21, 2014, which a national filing of PCT Application Serial No. PCT/IB2012/054434, filed Aug. 29, 2012, published as WO 2013/035015A1 on Mar. 14, 2013, which claims the benefit of U.S. Provisional Application Ser. No. 61/531,683, filed Sep. 7, 2011, which is incorporated herein by reference.

FIELD OF THE INVENTION

The invention relates to a device and method for supporting operating displaying image data, wherein the image data may change over the time.

BACKGROUND OF THE INVENTION

When image data has been generated, the generated image data may be stored in a storage. When displaying the (previously) generated image data, a double buffering of the image data may be performed: one buffering is done in the previous storage, which has been used after generating the image data, and other buffering is done for displaying the image data. When changing image data is generated, i.e. image data, visible contents of which change over the time, and if the changing image data is displayed, it may happen that the displaying device displaying the changing image data does not retrieve the current image content of the displayed changing image for several reasons. In such a case, operating displaying the image data is executed incorrectly. As a consequence, an operator or user, which watches the image data displayed by the displaying device, may not recognize that something is wrong, especially, when the displayed image is almost static (i.e. only some parts of the image change and/or the changes occur with large intervals). In other case, the operator or user may have a short glance at the displayed image, which is not long enough to recognize that nothing is changing, and, therefore, does not recognize the false operating of the displaying the image data.

An incorrect or erogenous operating displaying images may become critical particularly in such cases when the currentness of the displayed data is important, for example, when the displayed images give information to the operator or user whether the situation visualized in the displayed image is critical or not, whether a particular handling is required with regard to a changed situation visualized in the displayed image. For example, at least one part of the image, a plurality of parts of the image or the whole image may show critical information like alarms, measured information, critical locations, information of interest or critical vital signs for a patient, for example. When at least one part of the image, a plurality of parts of the image or the whole image changes over the time, a correct displaying of the image by considering and visualizing the changes is mandatory and probably vitally important.

The known solutions for displaying such changing image data, which may be critical and may be relevant to security, still do not provide reliable displaying of the image data, particularly, a reliable displaying of the image data if it changes. Hence, a need for solutions enabling a correct operating of displaying image data is still present.

SUMMARY OF THE INVENTION

It is an object of the present invention to provide a solution for a reliable operating of displaying image data, by use of which it is ensured that current image data is displayed, i.e. that the displaying is done correctly.

The invention is based on the idea that additional information is added to image to be displayed, wherein the additional information may be invisible or nearly invisible when the image comprising the additional information is displayed, and that the additional information is used for monitoring the currentness of the displayed image, which, particularly, displayed contents of which may change over the time. The monitoring may be an independent process or part and is used to check integrity of changing image data, which may be critical. The additional information, particularly, the content of the additional information may be independent from the image, particularly, from the content visualized by the image. The additional information incorporated in the image may be changed over the time. Monitoring the displaying of the image may be done by checking the additional information with regard to additional information expected to be present in the displayed image. If the additional information has been changed or updated over the time, the expected additional information has to correspond to the last changed or updated additional information for approving a correct operating the displaying of the image. Further, the present invention may allow integrating changed image parts, which are retrieved or derived by other image sources, into the image to be displayed, wherein the other image sources are not the original image source of the image combined with additional information and may provide image data, which lacks, i.e. does not comprise additional information.

The present invention may be utilized in several areas, where displaying of image data is done, for example, in the area of medical technology, where data of patients comprising measured values and/or captured image data are displayed for monitoring conditions of the patients and where the data is displayed as images and may change over the time. The present invention is not restricted to a specific area of use.

In one aspect of the present invention, a device is provided, which is arranged for supporting operating displaying image data, wherein the image data may change over the time, said device being configured to: generate a secured image based on a source image by generating at least one secured image part, wherein the secured image part is generated by combining a source image part of the source image with a corresponding secure pattern; and/or monitor displaying the secured image by detecting the corresponding secure pattern of the secured image part and by performing at least one of following: updating the detected secure pattern, checking the currentness (i.e. correctness) of the detected secure pattern. Secure patterns combined with source image parts correspond to the above-mentioned additional information. The monitoring is performed with regard to secured image as displayed. Thus, detecting, updating and checking secure patterns is done by detecting, updating and checking secure patterns in displayed secured image. By use of the present invention, a continuous, effective and fast monitoring operating of displaying image data is ensured, which enables a fast recognition of wrong and/or erroneous operating displaying image data and may be used for solving the false operating. Further, the implementation of the present invention may be done independently of the source of the image data and allows monitoring displaying image data, which may have several sources, as in the monitoring operation of the device just the secure patterns representing the above-mentioned additional information are checked without an explicit need for considering the visualized content of the image. The image itself comprises several image parts, visualized or displayed content of which may have several sources. Thus, a flexible monitoring operating of displaying image data is enabled.

According to an embodiment of the present invention, the device is configured to generate the secured image by dividing the source image into a plurality of source image parts and by adding the corresponding secure pattern to at least one of the divided source image parts. Thus, the device allows a flexible implementing of monitoring displaying image data allowing use of different sizes of image parts and different arrangements of secure patterns. The secure patterns may be added to each source image part, to some source image parts, to one source image part. Thus, a flexible building or configuring of image to be displayed comprising image parts having several sources is supported, since some sources of some image parts may not use integrating secure patterns whereas other sources do.

According to an embodiment of the present invention, the source image part of the source image is a tile. Thus, also the secured image parts will be tiles.

According to a further embodiment of the present invention, at least two image parts of secured image may overlap. This may be particularly true for secured images having image parts originating from several sources, each of which may update just specific portion(s) or part(s) of the secured image.

According to an embodiment of the present invention, the corresponding secure pattern represents at least one of following a digital watermark, a hidden information. Thus, a flexible and variable implementing of the present invention is supported.

According to an embodiment of the present invention, the corresponding secure pattern comprises at least one of the following: information allowing identification of currentness of the secured image part; information allowing synchronization of the secured image part; information allowing determining a source of the secured image part; position information of the secured image part; information allowing detecting the secure pattern of the secured image part; information indicating content of the secured image part when displayed. To this, it has to be noted, that the present invention is not restricted to the above mentioned contents of a secure pattern only and that a secure pattern may comprise also further useful information, which will be apparent to the skilled person in dependence of environment of implementing the present invention.

According to an embodiment, the information allowing identification of currentness of the secured image part comprises at least one of following: a time information, a sequence counter; the information allowing synchronization of the secured image part comprises at least one of following: a sync signal, a start sequence, a checksum signal, an end sequence; the information allowing determining the source of the secured image part comprises a source identifier; the position information of the secured image part comprises at least one of following: a unique index of the image part, a position of the image part in the image; and/or the information indicating the content of the secured image part when displayed comprises at least one of the following: a hash of the displayed data of the secured image part, a checksum of the displayed data of the secured image part, a hash of the displayed pixel values of the secured image part, a checksum of the displayed pixel values of the secured image part. Also to this, it has to be noted, that the present invention is not restricted to the above mentioned contents only and that a secure pattern may comprise also further useful information, which will be apparent to the skilled person in dependence of environment of implementing the present invention.

According to an embodiment of the present invention, the device is configured to generate the secured image by encoding the corresponding secure pattern (in the source image part for generating the secured image part). According to a further embodiment, the encoding of the corresponding secure pattern comprises encoding the corresponding secure pattern in at least one of least significant bits of the source image part (for generating the secured image part) and/or encoding the corresponding secure pattern in at least one of most significant bits of the source image part (for generating the secured image part). When the secure pattern is encoded in at least one of least significant bits, the visibility of the secure pattern may be reduced or avoided when displaying the secured image. When the secure pattern is encoded in at least one of most significant bits, the secure pattern may be made visible when displaying the secured image. Thus, a flexible implementation of the present invention in dependence of requirements of the environment and purpose of the implementation is supported.

According to an embodiment, the device is configured to generate the secured image by performing redundant encoding of the corresponding secure pattern (in the source image part).

According to a further embodiment of the present invention, the device is configured to detect the corresponding secure pattern by scanning at least one certain row, at least one certain column and/or at least one certain tile of the secured image for an information indicating a possible presence of a secure pattern. Also in this way, a variable and flexible implementation of the present invention is enabled. Further, the detecting of the secure patterns may be performed in a fast way and without wasting (storage) resources. The scanning may be performed with regard to secured image as displayed.

According to an embodiment, the device is configured to store the corresponding secure pattern of the secured image part. Thus, a reliable monitoring operating of displaying images is supported, as it may be ensured that all secure patterns necessary for the monitoring may be taken into consideration.

According to a further embodiment, the device is configured to store the updated secure pattern of the secured image part. Thus, a continuous reliable monitoring operating of displaying images is supported, as it may be ensured that all secure patterns necessary for the monitoring may be taken into consideration and that the examination of their currentness or correctness respectively will be done correctly and reliably.

According to an embodiment of the present invention, the device is configured to check the currentness of the detected secure pattern by comparing the detected secure pattern with an expected current secure pattern. The expected current secure pattern will correspond to the last added or updated secure pattern. If the device is configured to store updated secure pattern(s), the expected current secure pattern may be the corresponding stored updated secure pattern.

According to a further embodiment of the present invention, if the checked secure pattern is not the expected current secure pattern, the device is configured to perform at least one of following: indicate that the secured image is not a current secured image, exit the displaying of the secured image, restart the displaying of the secured image. Here, also further appropriate actions are possible, which will be apparent to the skilled person in view of environment and conditions of implementation of the present invention.

According to an embodiment of the present invention, if no secure pattern is detected in the secured image, the device is configured to perform at least one of following: indicate that the secured image does not meet security requirements, exit the displaying of the secured image. In this way, the present invention may be implemented to recognize or detect images of unreliable sources. Usually, images of unreliable sources will not comprise additional information like security pattern(s). Thus, the present invention enables monitoring operation of displaying images by taking into consideration security requirements set out at least with regard to displayed images.

According to an embodiment, the device is configured to perform the checking: at a certain point of time; and/or after transmitting an information to a displaying device, which displays the secured image, wherein the information indicates a request for providing the secured image as currently displayed, and receiving the secured image as currently displayed.

According to an embodiment of the present invention, the device is configured to perform the monitoring with regard to the secured image as stored for displaying, with regard to the secured image as transmitted for displaying and/or with regard to the secured image as detected from a displaying device, which displays the secured image. By implementing several ways of access to the image to be displayed, the reliability of the monitoring is increased.

In a further aspect of the present invention, a method for supporting operating of displaying image data is provided, wherein the image data may change over the time, said method comprising: generating a secured image based on a source image by generating at least one secured image part, wherein the secured image part is generated by combining a source image part of the source image with a corresponding secure pattern; and/or monitoring displaying the secured image by detecting the corresponding secure pattern of the secured image part and by performing at least one of following: updating the detected secure pattern, checking the currentness of the detected secure pattern. In general, the method is configured to perform the operations of the device as outlined above and as described in more detail below. Thus, also by the provided method, all of the effects described with regard to the device may be achieved and vice versa.

Thus, the present invention involves a concept to generate secured images or secured image streams that can be monitored for integrity and timely updates. The present invention suggest supporting operating of displaying image data and, particularly, the monitoring of the displaying, as a reliable process that renders critical or safety relevant data into a critical or secured image. Further, the present invention allows also monitoring displaying of image data, which may be combined with other image data from unknown and/or unreliable sources.

DETAILED DESCRIPTION OF THE EMBODIMENTS

As can be derived from the aforesaid, a purpose of a display, e.g. a patient monitor, is to show critical data undistorted, without obscuring and in a timely manner. I.e., it is critical that certain parts of an image, e.g. areas showing alarms or critical vital signs, which may change over the time, are fully visible and updated regularly. For ensuring an effective, fast and safe operating of displaying of image data, which comprise information being relevant to safety, which may change over the time and/or displaying of which has to be up to date (i.e., if changes of at least one part of the image have occurred, these changes have to be visualized, displayed immediately), a secured image is generated by adding (invisible) information to a source image, i.e. information, which is not displayed and/or which is not visible or is almost invisible when displaying the corresponding image. This information may be seen as security pattern(s). Further, instead of the source image, the secured image is displayed, wherein the currentness of the displayed secured image is checked by use of the added (invisible) information like the security pattern(s). The added (invisible) information like the security pattern(s) is updated from time to time. Thus, if operating of displaying the secured image is executed correctly, the displayed secured image has to comprise the current added (invisible) information like the current security pattern(s), i.e. the current added (invisible) information or current security pattern(s) last amended.

Figure 1:
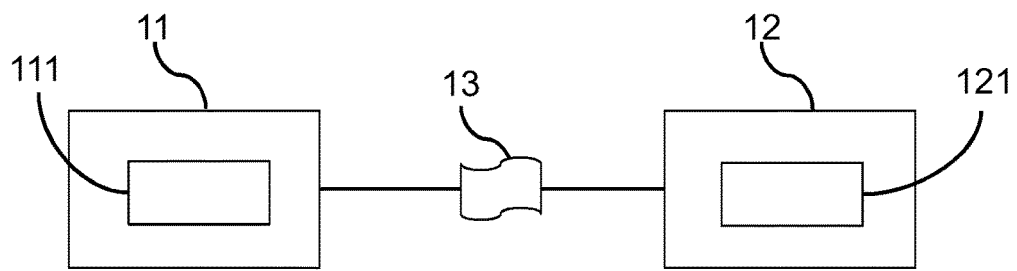
FIG. 1 illustrates an arrangement or system of devices configured to execute or support the monitoring of displaying image data according to an embodiment of the present invention.

FIG. 1 illustrates an arrangement or system of devices 11, 12 configured to execute or support the monitoring of displaying image data according to an embodiment of the present invention. According to the present embodiment, two devices 11 and 12 are provided, wherein the first device 11 is an image generating device and the second device 12 is a monitoring device 12. According to the present embodiment, the image generating device 11 may be configured to detect a source image (e.g. to generate, obtain, recognize a source image). Further, the image generating device 11 is configured to generate a secured image 13 based on the source image by combining the source image with (invisible) information. Particularly, according to the present embodiment, to this, to at least one part of the source image a corresponding security pattern is added. The generating of the secured image may be performed by an secured image generator 111, which may be a software and/or hardware device, entity, component or system comprised in the generating device 11. According to the present embodiment, the generated secured image 13 (comprising image data of the source image combined with the (invisible) information or security pattern(s)) is provided (e.g. transmitted) by the image generating device 11 for displaying purposes. The generated secured image 13 may be, for example, be stored in a storage like frame buffer, from which the images to be displayed are taken by a displaying device, or be provided (directly or indirectly) to the displaying device, e.g. in form of a data stream like a video stream for example. to the monitoring device 12. The monitoring device 12 is configured to access the displayed secured image 13. Particularly, the monitoring device 12 is configured to update the (invisible) information or security pattern(s) for monitoring the operating of displaying the secured image 13. Further, the monitoring device 12 is configured to check the currentness of the displayed secured image 13 by use of the (invisible) information or security pattern(s) for monitoring the operating of the displaying the secured image 13. For the monitoring purposes, the monitoring device 12 may comprise an (displaying operation) observer 121, which may be a software and/or hardware device, entity, component or system comprised in the monitoring device 12. The devices 11, 12 may be software and/or hardware devices, entities, components or systems.

Figure 2:
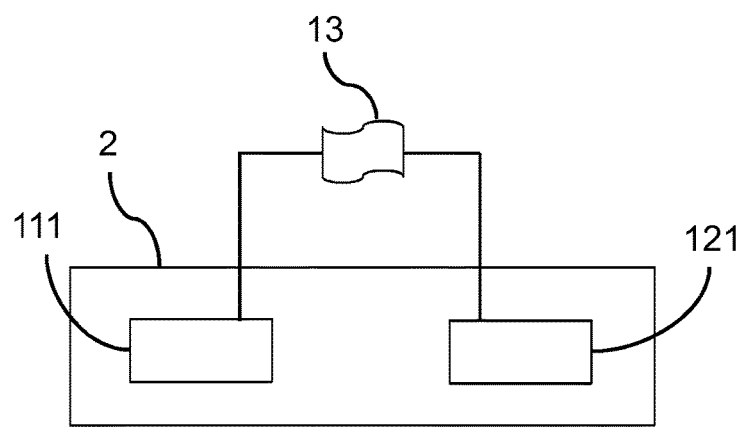
FIG. 2 illustrates an a device configured to execute or support the monitoring of displaying image data according to an embodiment of the present invention.

FIG. 2 illustrates an arrangement a device 2 configured to execute or support the monitoring of displaying image data according to an embodiment of the present invention. According to the present embodiment one device 2 is configured to execute the operations of the above outlined image generating device 11 and the monitoring device 12 as outlined above. I.e., only one device 2 is configured to perform or support monitoring displayed images, thus, to perform the monitoring of correctness of operation of displaying image data. To this, the device 2 may comprise a secured image generator 111, which may be configured as outlined above, and an (displaying operation) observer 121, which may be configured as outlined above. The device 2 may be a software and/or hardware device, entity, component or system.

Figure 3:
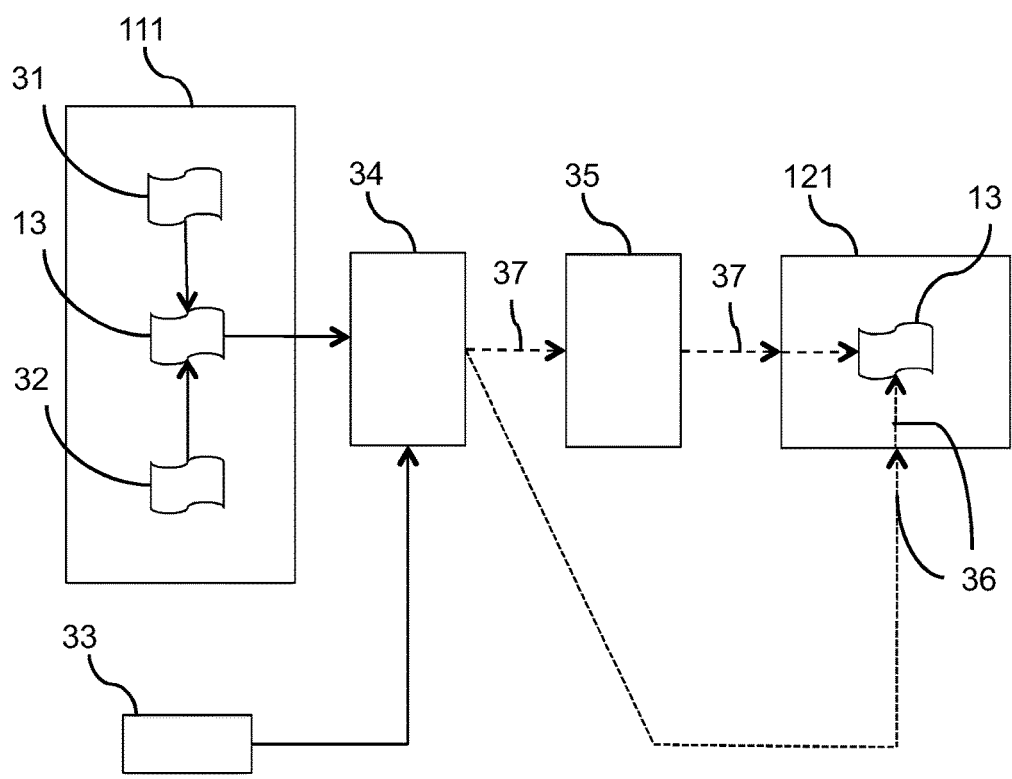
FIG. 3 illustrates an arrangement for executing or supporting the monitoring of displaying image data according to an embodiment of the present invention.

FIG. 3 illustrates an arrangement for executing or supporting the monitoring of displaying image data according to an embodiment of the present invention. The arrangement of the present embodiment comprises the secured image generator 111 and the observer 121, which may be comprised in two separate devices 11, 12 as shown in FIG. 1 or in one device 2, as shown in FIG. 2.

Usually, an image source renders image information and then writes it into a storage like a frame buffer, for example, for displaying the image information. This usual case is shown by components or entities 33 and 34, where the component 33 is a conventional image source and the component 34 is storage like a frame buffer, for example, and where the image source 33 writes image information or data, rendered or generated by the image source 33, into the frame buffer 34.

According to the present embodiment, the secured image generator 111 is a secured image source and is configured to execute a reliable process that renders critical data, which comprise information being relevant to safety, which may change over the time and/or displaying of which has to be up to date (i.e., if changes of at least one part of the image have occurred, these changes have to be visualized, displayed immediately), into a critical source image 32. However, before writing the source image 32 into the frame buffer 34, according to the present embodiment, the secured image generator 111 executes the reliable process by generating or rendering at least one secure pattern 31 that is combined or overlaid with the source image 32 thereby yielding or generating a secured image 13. This secured image 13 is then written into the frame buffer 34.

According to the present embodiment, the frame buffer 34 may store also other images, which are generated by other image sources 33, besides the secured images 13, which are generated by the secured image generator 111. In such a case, such other images may be stored or positioned in the storage or frame buffer 34 such that they do not overlay or otherwise disturb the secured images 13.

According to the present embodiment and also according to further embodiments of the present invention, in order to not disturb the user when the user views the displayed secured image 13, the secure pattern(s) may be kept unperceivable or invisible. To this, known techniques like steganography or watermarking may be used with regard to the secure pattern(s).

If the storage or frame buffer 34 is the final storage or frame buffer before displaying, i.e., if the images displayed by a displaying device is taken from the storage or frame buffer 34, according to the present embodiment, the (displaying operation) observer 121 is configured to take the secured image 13 from the storage or frame buffer 34 for performing the monitoring of displaying the secured image 13 by the displaying device. This case is visualized by arrows 36 in FIG. 3.

However, if at least one further storage or frame buffer 35 is used for storing the secured image 13, i.e., if the images displayed by the displaying device is taken from a further storage or frame buffer 35 as a final storage or frame buffer, according to the present embodiment, the observer 121 is configured to take the secured image 13 from the further storage or frame buffer 35 as the final storage or frame buffer for performing the monitoring of displaying the secured image 13 by the displaying device. This case is visualized by arrows 37 in FIG. 3.

In general, if the displaying device is configured to take a secured image 13 from a storage or frame buffer 34, 35 for displaying the secured image 13, the observer 121 can read out the secured image 13 out of the final frame buffer 34, 35 and can extract the added (invisible) information 31 like the security pattern(s) and, subsequently, update the (invisible) information or security patterns 31 and/or decide, which image parts of the secured image 13 are displayed correctly, i.e., whether the current secured image 13 or the current secured image parts respectively are displayed by the displaying device.

Figure 4:
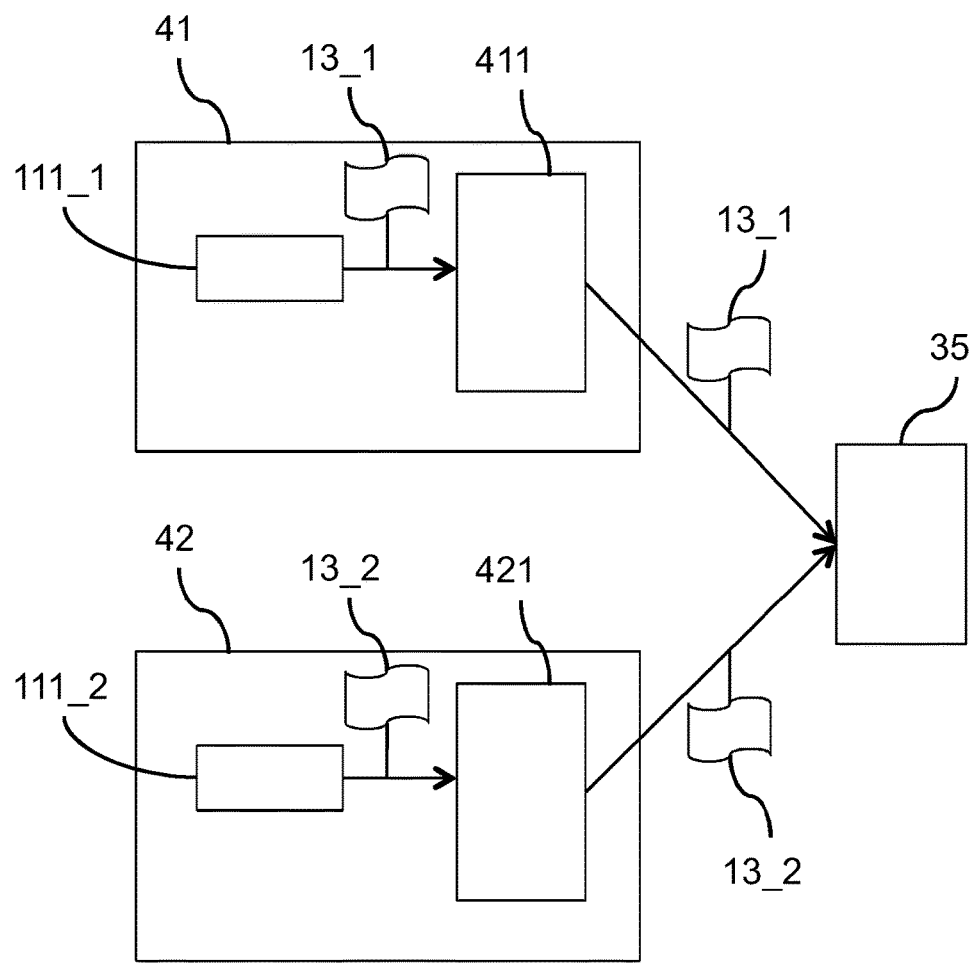
FIG. 4 illustrates an arrangement for executing or supporting the monitoring of displaying image data according to an embodiment of the present invention.

FIG. 4 illustrates an arrangement for executing or supporting the monitoring of displaying image data according to an embodiment of the present invention. According to the present embodiment, two devices 41, 42 are given, each of them comprising its own secured image generator 111_1, 111_2, which is configured according to the present invention, and its own storage or frame buffer 411, 421, wherein the corresponding storage or frame buffer 411, 421 is configured to store the corresponding secured image 13_1, 13_2 generated by the corresponding image generator 111_1, 111_2. The generated secured images 13_1 and 13_2 are subsequently stored in the final storage or frame buffer 35, from which the secured images 13_1 and 13_2 are taken for displaying them by the displaying device and from which the images 13_1 and 13_2 are used by the observer 121 for monitoring purposes. Each of the devices 41, 42 may be a software and/or hardware device, entity, component or system. Additionally, it has to be noted that the present embodiment shows two devices 41, 42 only for sake of a better understanding and that the present invention allows also the use of more than two devices 41, 42 (i.e. a plurality of devices) in a similar way. Thus, the present invention effectively allows monitoring operating of displaying secured images, which originate from several sources or devices 41, 42 respectively.

Figure 5:
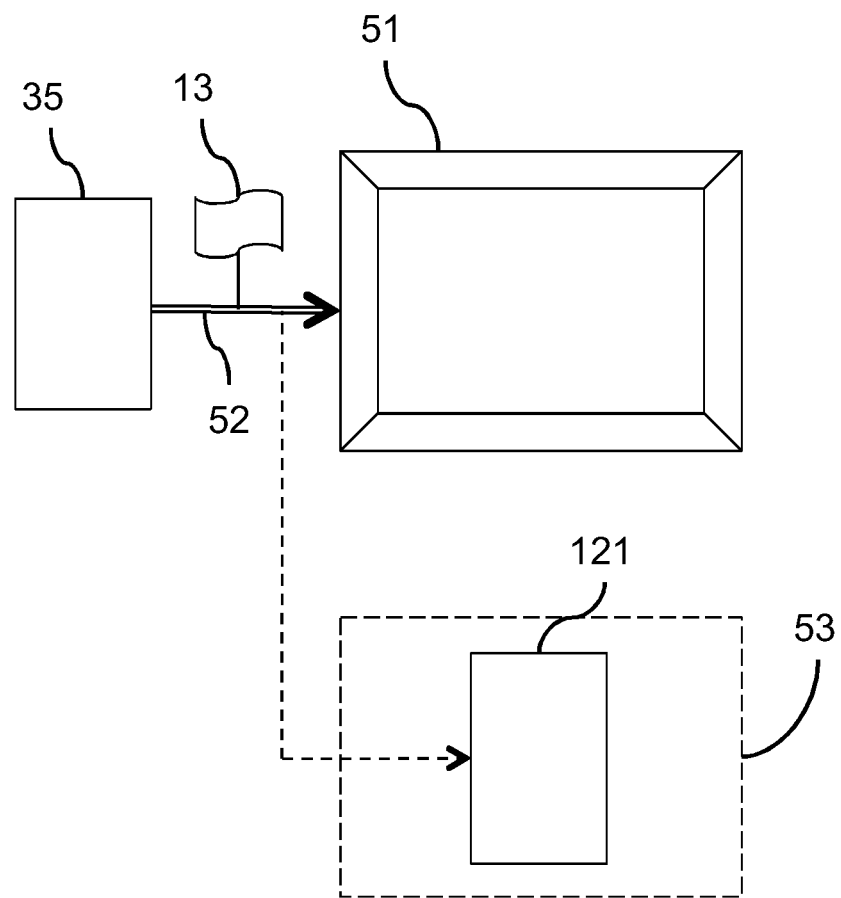
FIG. 5 illustrates an arrangement for executing or supporting the monitoring of displaying image data according to an embodiment of the present invention.

FIG. 5 illustrates an arrangement for executing or supporting the monitoring of displaying image data according to an embodiment of the present invention. According to the present embodiment, the observer 121 is configured to take the secured image 13 for monitoring purposes from an image transmitter 52, which provides the secured image 13 to the displaying device 51 for displaying the secured image 13. The image transmitter 52 may be, for example, a video stream (e.g. on the video cable to the display device 51) or other appropriate image transmitter 52, which the skilled person will and can recognize as provider or transmitter of image data for displaying purposes. The image transmitter 52 may be outside and/or inside the displaying device 51. According to the present embodiment, the image transmitter 52 such as video stream transmits a secured image 13, which the image transmitter 52 has received directly or indirectly from a final storage 35 such as frame buffer. Thus, the secured image 13 to be displayed can be tapped and used for monitoring the operation of the displaying the secured image 13 by the observer 121. The observer 121 may detect, update and/or analyze the information of the secured image 13 on the fly or by using a frame grabber hardware and/or software, which puts the information into a frame buffer, which, in turn, can be accessed by the observer 121 for monitoring purposes. A secured image taper enabling taping of the secured image 13 from the image transmitter 52 may be a separate device, entity, component or system or may be combined in the sourcing device. The secured image taper may also be a part of the observer 121, or, if the observer 121 is located in a further device 53, the secured image taper may also be a part of the device 53 comprising the observer 121. An observer 121 that is built in hardware can be, for example, implemented in an ASIC (Application Specific Integrated Circuit) of FPGA (Field Programmable Gate Array), especially, if such hardware is used anyhow to generate a video stream 52 for providing the secured image 13 to the displaying device 51 for displaying purposes. In this way, the present embodiment of the present invention enables monitoring the operating of the displaying of the secured image 13 also if the final storage or frame buffer 34, 35 cannot be reliably recognized or identified by the observer 121, e.g., because the graphical sub-system is unknown or too complicated to be analyzed. Additionally, the present embodiment of the present invention enables a reliable capturing of secured images 13 to be actually displayed by the displaying device 51.

Here, it has to be noted that an observer 121 may be configured to retrieve a secured image 13 also in both ways by use of a final storage or frame buffer 34, 35 and by use of an image transmitter 52 such as video stream. In this case the observer 121 may decide on the appropriate way of retrieving the secured image 13 to be displayed, for example, by considering several retrieving conditions like reliability of the retrieved secured image 13 to be displayed, for example. The skilled person will be able to recognize the appropriate retrieving conditions in dependence on implementation environment of the present invention.

Figure 6:
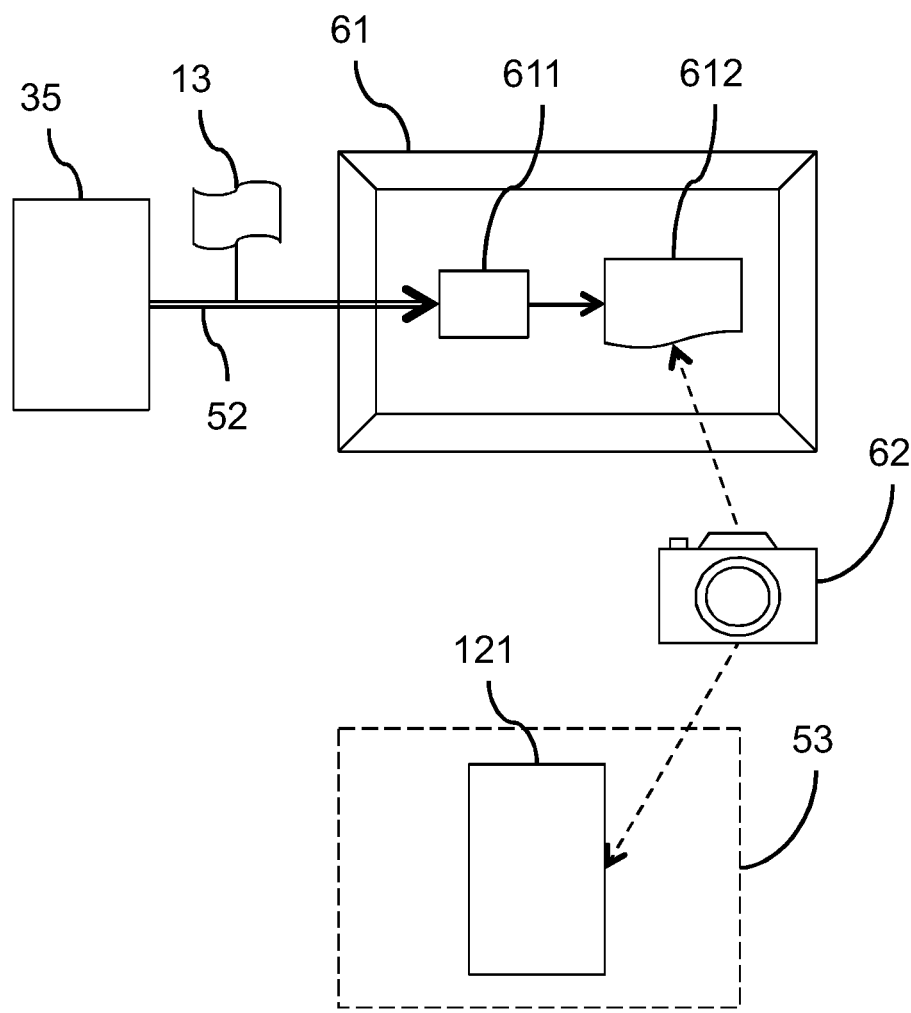
FIG. 6 illustrates an arrangement for executing or supporting the monitoring of displaying image data according to an embodiment of the present invention.

FIG. 6 illustrates an arrangement for executing or supporting the monitoring of displaying image data according to an embodiment of the present invention. According to the present embodiment, the displaying device 61 comprises a storage 611, which captures the data transmitted by the image transmitter 52 such as video stream. Thus, the storage 611 captures or receives the secured image 13. The secured image 13 is stored in the displaying device 61 or the storage 611 respectively. Then, the displaying device 61 transforms the secured image 13 (as stored), wherein the displaying device 61 adapts the display format (e.g. size, aspect ratio, frame rate or image enhancement methods) of the secured image 13 and, thus, generates a secured displayed image 612. This secured displayed image 612 is then the image, which is actually displayed by the displaying device. In this case, when the displaying device 61 amends the secured image 13, which has been received for displaying, i.e., generates a corresponding secured displayed image 612 based on the secured image 13, the displaying device 61 considers it as being an unreliable displaying device 61. According to the present embodiment, for executing a correct monitoring of operating displaying the secured image 13, an image recording device 62 like a camera, for example, monitors the secured displayed image 612, which is actually displayed by the displaying device 61. The recorded images, which have been recorded or monitored by the image recording device 62, represent the secured displayed image 612. The image recording device 62 transmits the recorded images (directly or indirectly) to the observer 121, which then can perform the monitoring based on the recorded images (e.g. either in hardware or via frame grabber in software as described with regard to FIG. 5).

Here, it has to be noted that an observer 121 may be configured to retrieve a secured image 13 also in at least one of the above-outlined ways by use of a final storage or frame buffer 34, 35, by use of an image transmitter 52 such as video stream, by use of the image recording device 62. Also to this, the observer 121 may decide on the appropriate way of retrieving the secured image 13 to be displayed, for example, by considering several retrieving conditions like reliability of the retrieved secured image 13 to be displayed or reliability of the displaying device, for example. The skilled person will be able to recognize the appropriate retrieving conditions in dependence on implementation environment of the present invention.

Figure 7:
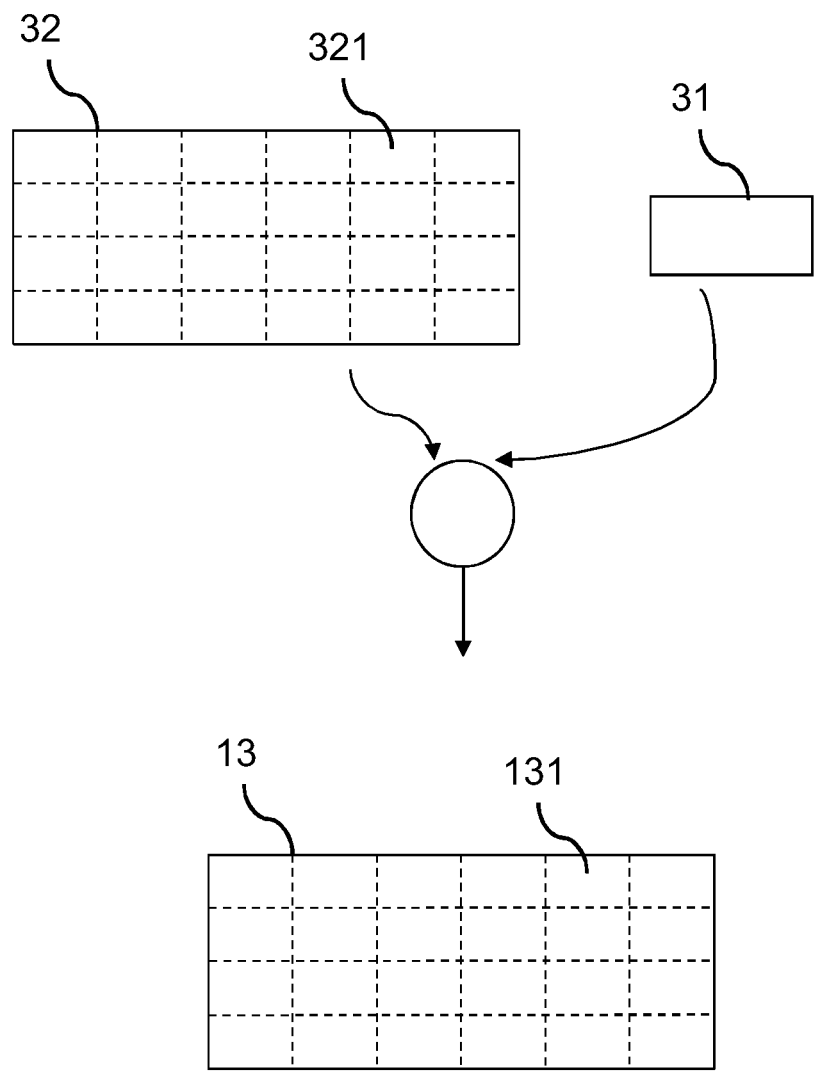
FIG. 7 illustrates generating a secured image according to an embodiment of the present invention.
Figure 8:
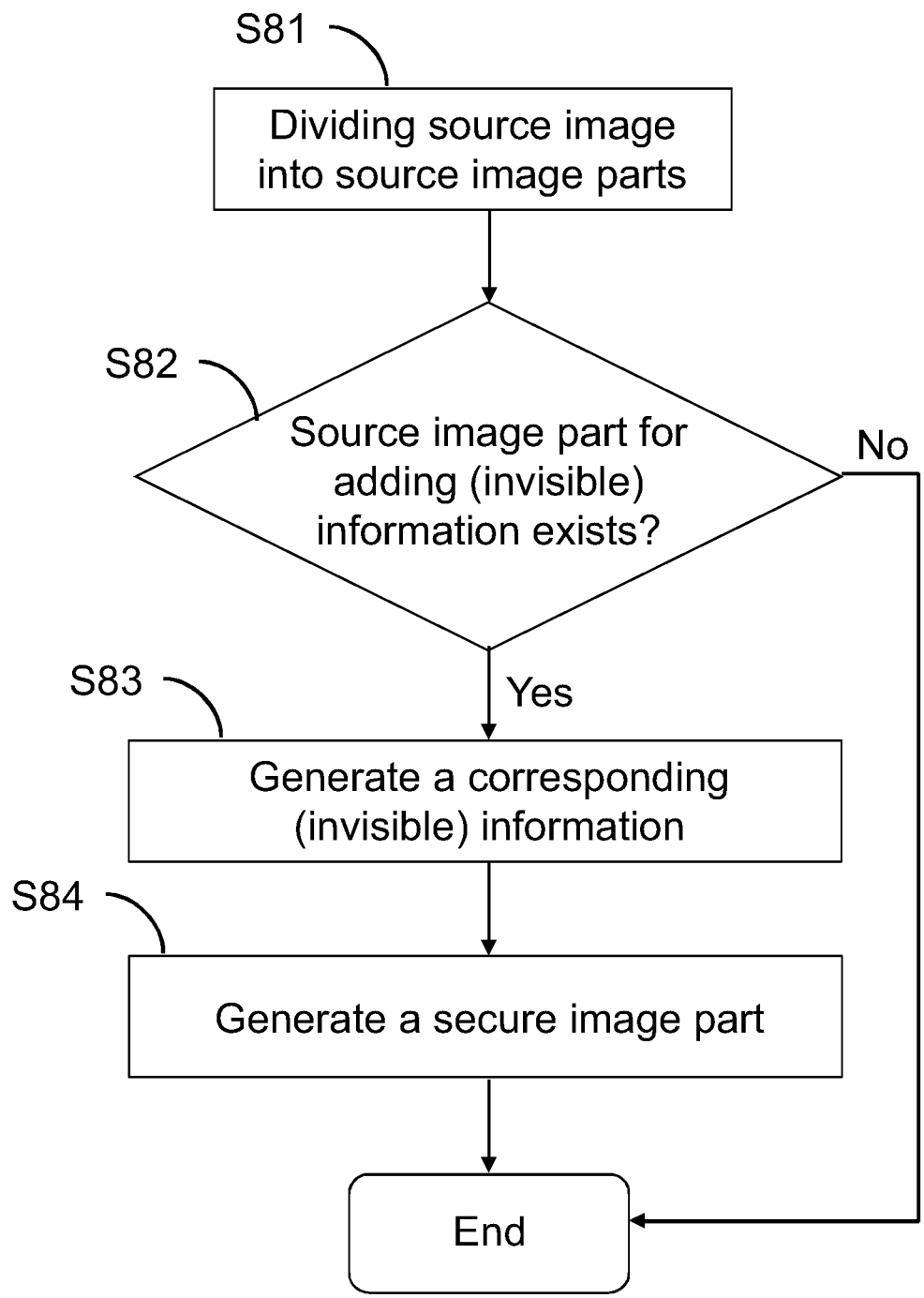
FIG. 8 illustrates steps or operations performed for generating a secured image according to an embodiment of the present invention.

In following, generating of a secured image 13 as performed according to an embodiment of the present invention will be explained in more detail by referring to FIGS. 7 and 8. The generating may be executed by a secured image generator 111 or by a further device configured to execute the corresponding operations. In following, for sake of clarity, the generating will be explained with regard to the above introduced secured image generator 111.

At first, in step S81 a source image 32 is divided into a plurality of source image parts 321 (i.e. at least one source image part 321). According to the embodiment of FIG. 7, the whole source image 32 is structured or divided into tiles 321, wherein the tiles 321 may be of a certain or predetermined size. For example, a source image 32 of size 1024×768 pixels may be structured or divided into tiles 321 of 64×16 pixels.

If S82 the source image 32 comprises a source image part or tile 321, to which a which an (invisible) information 31 (i.e. information, which is not displayed, like a security pattern 31), should be added, in step S83 a corresponding (invisible) information or security pattern 31 respectively is generated for the source image part or tile 321. The (invisible) information or security pattern 31 may comprise at least one of the following: information allowing identification of currentness of the resulting secured image part 131 (e.g. a time information, a sequence counter), information allowing synchronization of the resulting secured image part 131 (e.g. a sync signal, a start sequence, a checksum signal and/or an end sequence), information allowing determining the source of the resulting secured image part 131 (e.g. a source identifier) so that it can be distinguishing between different image or image part sources, position information of the resulting secured image part 131 (e.g. a unique index of the image part and/or a position of the image part in the image), information allowing detecting the (invisible) information or secure pattern 31 of the resulting secured image part 131, wherein this information may increase the performance of detecting the (invisible) information or secure pattern 31, information indicating content of the resulting secured image part 131 when displayed (e.g. a hash of the displayed data of the secured image part 131, a checksum of the displayed data of the secured image part 131, a hash of the displayed pixel values of the secured image part 131, a checksum of the displayed pixel values of the secured image part 131).

In step S84, the corresponding (invisible) information or security pattern 31 is combined with the source image part or tile 321. Thus, in step S84, a corresponding secured image part 131 of the secured image 13 is generated by said combining. For example, the combining is performed by adding the corresponding (invisible) information or security pattern 31 added to the source image part or tile 321. To this, the (invisible) information or security pattern 31 may be encoded, for example, in at least one last significant bit of the source image part or tile 321 to achieve least perceptibility or visibility of the resulting secured image part 131. The (invisible) information or security pattern 31 may be encoded also in at least one most significant bit of the source image part or tile 321. Further, for combining, in step S84, additional redundant encoding may be used to improve robustness of the integrity check. E.g. only certain combinations of last significant bits for the RGB (Red, Blue, and Green) channels may be used. Redundant encoding (e.g. alternate codes) may be used to randomize otherwise potentially regular patterns, which are more perceptible by the user.

In step S84, the corresponding (invisible) information or security pattern 31 is combined with the source image part or tile 321 and written into the frame buffer 34, 35, 411, 421.

Thus, the resulting or generated secured image 13 corresponds to the source image 32, comprises the same image parts 321, wherein at least one of the image parts 321, as comprised in the source image, is combined with a corresponding (invisible) information or security pattern 31 and forms a corresponding secured image part 131 of the resulting or generated secured image.

Figure 9:
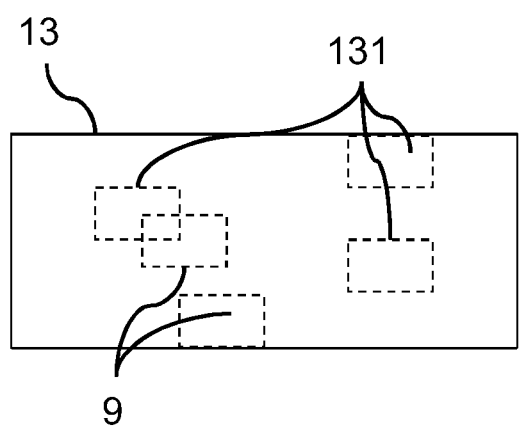
FIG. 9 illustrates a secured image generated according to an embodiment of the present invention.

Another processes or devices 33 may write other images into the same frame buffer 34, 35, 411, 421 and, thereby, overwrite or otherwise modify the secured image 13. FIG. 9 illustrates a secured image 13 generated according to an embodiment of the present invention, wherein the secured image 13 comprises secured image parts 131 and other image parts 9 generated by other processes or devices 33. The other image parts 9 may be parts generated after generating the secured image 13 and may represent current image part information, which updates the previous image part information of the secured image 13. Thus, the secured image 13 may comprise at least one secured image part 131, which is combined with a corresponding (invisible) information or security pattern 31, and at least one other image parts 9 with or without a corresponding (invisible) information or security pattern 31. The secured image parts 131 or at least one secured image part 131 may be overlaid, obscured and/or otherwise modified by other image parts 9 or at least one other image part 9.

The observer 121 analyzes then the content of image parts 131, 9 of the secured image 13 and ignores image parts 131, 9 that contain no secure pattern 31 or a corrupted pattern. Valid secure patterns 31 may comprise a correct sync/start sequence and end sequence and a valid checksum. They may contain as well only valid codes (if redundant coding is used). The observer 121 may extract from valid secure patterns 31 the source ID (identification), sequence counter (or time info) and the position info. Using the source ID, the observer 121 can distinguish image parts 131, 9 that were generated by different (potentially independent) secured image sources. The observer 121 may check the information regarding the position of the image part 131, 9 and, thereby, detect whether parts 131, 9 were moved elsewhere on the screen of the displaying device 51, 61 that may result in false interpretation by the user.

Figure 10:
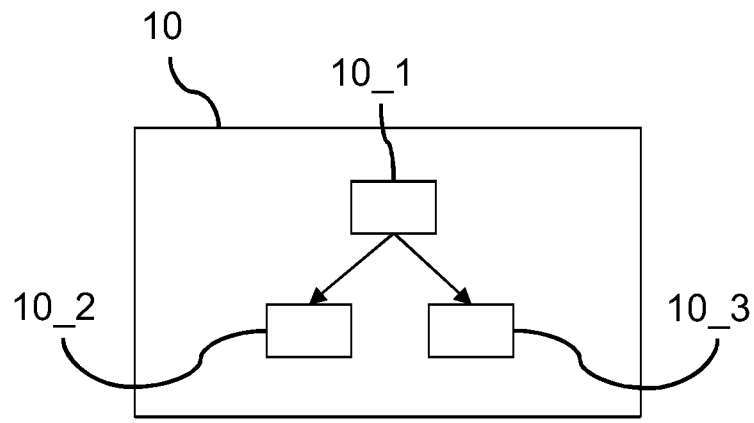
FIG. 10 illustrates an overview of monitoring displaying a secured image according to an embodiment of the present invention.

The monitoring of the operating of displaying a secured image may be divided into two parts updating at least one (invisible) information or security pattern 31 of the secured image 13, checking the currentness or correctness of the at least one (invisible) information or security pattern 31 of the secured image 13, wherein the updating and the checking may be performed independently from each other. FIG. 10 illustrates an overview of the monitoring of the displaying a secured image according to an embodiment of the present invention, wherein the monitoring process 10 comprises three sub-processes: detecting process 10_1, in which the at least one (invisible) information or security pattern 31 of the secured image 13 is detected; updating process 10_2, in which the at least one (invisible) information or security pattern 31 of the secured image 13 is updated; and checking the at least one (invisible) information or security pattern 31 of the secured image 13, in which the at least one (invisible) information or security pattern 31 of the secured image 13 is checked with regard to its currency or correctness respectively. At first the detecting sub-process 10_1 is performed and, subsequently, in dependence of the current situation of monitoring, the updating process 10_2 and/or the checking process 10_3 is executed.

The monitoring process 10 and its sub-processes are executed by the observer 121. To this, the observer 121 may comprise correspondingly arranged components, devices, entities or systems, which may be hardware and/or software.

Figure 11:
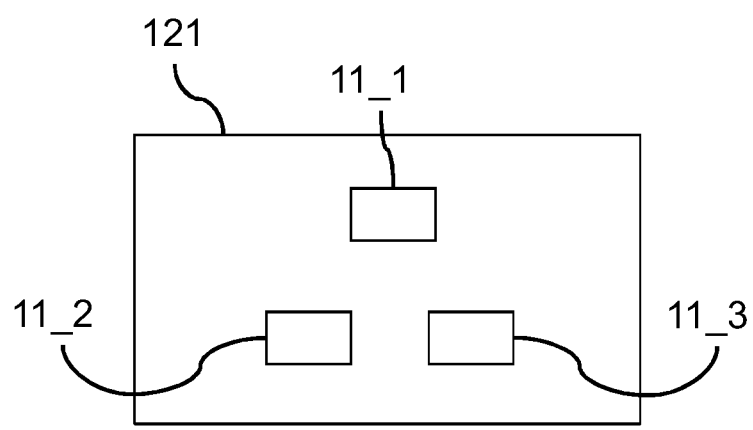
FIG. 11 illustrates an arrangement of an observer according to an embodiment of the present invention.

FIG. 11 illustrates an arrangement of an observer 121 according to an embodiment of the present invention. According to the embodiment of FIG. 11, the observer 121 comprises a detector (component, device, entity or system) 11_1, an updater (component, device, entity or system) 11_2 and a checker (component, device, entity or system) 11_3, wherein the detector 11_1 is configured to execute the detecting 10_1, the updater 11_2 is configured to execute the updating 10_2 and the checker 11_3 is configured to perform the checking 10_3.

In general, the updating sub-process 10_2 or the updater 11_2 updates or changes the at least one (invisible) information or security pattern 31 of the secured image 13 at certain point(s) of time (e.g. periodically) and/or after receiving the secured image 13, 612 as displayed by the displaying device and the monitoring sub-process 10_3 checks the currency or correctness of a detected (invisible) information or security pattern 31 of the secured image 13, 612.

If the (invisible) information or security pattern 31 is changing over the time and the checking sub-process 10_3 or the checker 11_3 detects that the (invisible) information or security pattern 31 is correct, i.e. corresponds to the last updated (invisible) information or security pattern 31, the operating of the displaying the secured image 13, 612 is performed correctly.

If no (invisible) information or security pattern 31 can be detected in the secured image 13, 612 as displayed by the detecting sub-process 10_1 of the detector 11_1, the source device 11, 2, 41, 42 and/or the secured image generator 111, 111_1, 111_2 may be inactive, i.e. may be in a state, in which no current secured images 13 or no secured parts 131 of the secured images 13 are generated.

If the detected (invisible) information or security pattern 31 does not correspond to the current, i.e. last updated (invisible) information or security pattern 31, the displaying device 51, 61 is not able to change the secured image 13, 612, when displaying it, according to the changed image information of the secured image 13. The displaying process of the displaying device 51, 61 may, for example, be frozen or a screenshot of the secured image 13 is shown. This represents a critical situation, since it can be expected that the operator or user will not notice this situation immediately when watching the displaying device 51, 61 and will make wrong decisions or perform wrong actions with regard to the displayed image.

The monitoring process 10 and thus, the observer 121, may be added to a given device or system 51, 61 for displaying images at different places. The monitoring process 10 and also the observer 121 may monitor the video signal 52 itself going to the display panel 51, 61. Such a monitoring process 10 and/or observer 121 may be implemented, for example, in hardware as a simple box in the video connection or can be placed in the display panel itself. Further, the monitoring process 10 and also the observer 121 may use the "final" storage or frame buffer 34, 35 of the system, i.e. use the memory, from which the secured image 13 to be displayed is taken and/or from which a corresponding video signal 52, which transmits the secured image 13 to the displaying device 51, 61, is generated. Thus, a memory is considered as representing a "final" storage or frame buffer 34, 35, if there is no memory behind that component, device, entity or system that is able to store a complete secured image 13. In this case, it is possible to search for the (invisible) information or security pattern 31 in the "final" storage or frame buffer 34. Moreover, the monitoring process 10 and/or observer 121 may be configured receive screen shots of the displayed secured image 13, 612 from another device, entity, component or system 62, which is configured to make screen shots of the displayed secured image 13, 612 in the displaying device 51, 61 and which is operated in parallel to the monitoring process 10 and/or observer 121. To this, it has to be noted, that the present invention allows arbitrary combining of the above outlined possibilities for executing the monitoring process 10 and implementing the observer 121.

In detecting sub-process 10_1 and/or by the detector 11_1, an (invisible) information or security pattern 31 is detected or sought. As the position of the (invisible) information or security pattern 31 is unknown, the complete secured image 13, 612 as displayed needs to be searched. Usually, it may be rather time consuming reading back data from the memory (e.g. "final" storage or frame buffer 34, 35), where the secured image 13, 612 as displayed is stored. Therefore, according to the present embodiment, only at least one certain row, at least one certain column and/or at least one certain tile or part of the secured image 13, 612 as displayed is sought or scanned for an (invisible) information or security pattern 31. Thus, for example, if the secure parts 131 of the secured image 13, 612 are tiles of height or 16 rows (of pixels), only every 16-th row (of pixels) is sought or scanned, since the secured image generator 111 has generated at least one an (invisible) information or security pattern 31 with regard to an image part 321, 131, which is a tile with a height of 16 rows. Scanning the certain row, column or time can detect that this is a "modulated noise", i.e. a fragment of a secured image part 131 comprising an (invisible) information or security pattern 31. In that case, the rows above and/or below likely contain fragments of an (invisible) information or security pattern 31 too. Therefore, the range of rows will be read back as well. If those fragments combine to a complete secured image part 131 with an (invisible) information or security pattern 31, the corresponding (invisible) information or security pattern 31 comprised in the secured image part 131 can be extracted or detected. In this way, the amount of memory or storage, that is needed to be read back, is optimized and is similar to amount of image data written by the application to be monitored.

Further, according to an embodiment, the same (invisible) information or security pattern 31 may be stored in multiple secured image parts 131, i.e. it can be still be monitored even if the output is partially obscured. For this reason, the (invisible) information or security patterns 31 as detected may be stored in a list. Additionally, also the number indicating how often the same (invisible) information or security pattern 31 has been found may be stored as a count attribute. Thus, the (invisible) information or security patterns 31 as detected may be secured in an (invisible) information or security pattern list.

According to an embodiment of the present invention, the detecting sub-process 10_1 and/or the detector 11_1 may be implemented in or as a software driver, which has access to the storage, where the secured image 13, 612 as displayed is stored.

Furthermore, as it may be likely that the complete information of the displayed image should not be read back (e.g. to preserve privacy or due to license terms) and exposed to an "external" application, using a list as described above may be preferred as no useful "real" image information is exposed.

When performing updating by the updating sub-process 10_2 and/or the updater 11_2, for example, the updating may be performed during displaying the secured image 13.

To this, the detected (invisible) information or security patterns 31 are updated or changed by changing the data comprised in the (invisible) information or security patterns 31. Thus, for example, information allowing identification of currentness of the secured image part 131 like time information, sequence counter, for example, may be changed. The updated (invisible) information or security patterns 31 may be stored in the (invisible) information or security pattern list, wherein a previous (invisible) information or security pattern 31 in the list is replaced or updated by the updated (invisible) information or security pattern 31. Further, the secured image 13 to be displayed is updated by replacing or updating the at least one (invisible) information or security pattern 31 by the corresponding updated at least one (invisible) information or security pattern 31. Then, for a correct operating of the displaying of the secured image 13, it is expected that the secured image 13, 612 as displayed comprises the updated at least one at least one (invisible) information or security pattern 31.

The updating may be performed, for example, at certain time point(s) (e.g. periodically). Thus, a continuous ensuring of correct operating of the displaying of the secured image 13 may be ensured. If the updating is executed periodically, the periods may be adapted or coordinated with regard to expected periods of occurrence of secured image 13 changes.

The checking sub-process 10_3 is executed and/or the checker 11_3 is operated during displaying the secured image 13. Here, it is checked whether the at least one (invisible) information or security pattern 31 detected in the displayed secured image 13, 612 is the last updated (invisible) information or security pattern 31. If the above-outlined (invisible) information or security pattern list is used, while checking an old and a new (invisible) information or security pattern list may be utilized, wherein the old (invisible) information or security pattern list comprises the (invisible) information or security pattern(s) 31 expected (e.g. lastly updated) and the new (invisible) information or security pattern list comprises the (invisible) information or security pattern(s) 31 detected for the checking. The (invisible) information or security pattern(s) 31 expected are compared with the (invisible) information or security pattern(s) 31 detected for the checking, e.g., by comparing the data comprised in the (invisible) information or security pattern(s). For example, the information allowing identification of currentness of the secured image part like time information, sequence counter, for example, may be compared. If an (invisible) information or security pattern 31 as detected for checking does not correspond to the corresponding (invisible) information or security pattern(s) 31 expected, the checking returns as result that the operating of the displaying of the secured image 13 is not executed correctly. The checking returns a negative result (i.e. indication that the operating of the displaying of the secured image 13 is not executed correctly) also when an (invisible) information or security pattern 31 expected in the displayed secured image 13, 612 is not detected (e.g. not comprised in the new list). Thus, a frozen displayed secured image 13, 612 can be detected.

According to the present invention, several reactions with regard to a negative output of checking may be performed.

According to an embodiment, the displaying of the secured image 13 may be restarted. This, reaction may work like a watchdog. To this, a communication from the checking sub-process 10_3, the checker 11_3 and/or the observer 121 to the displaying device 51, 61 may be implemented to transmit an indicator indicating that the displaying is not performed correctly and that a restart of the displaying is required. Subsequently, after receiving the indicator, the displaying device 51, 61 can restart the displaying of the secured image 13.

According to an embodiment, it is also possible to embed information in the displayed image 13, 612 so that an operator or user watching the displayed image 13, 612 will notice that something is wrong. In this case, it is still possible to try to reset the system, maybe after a short grace period where the operator or user might try to solve the problem of displaying.

According to a further embodiment, instead of embedding information into the displayed image 13, 61, it is also possible to blank the displayed image, i.e. to display nothing at all or otherwise modify the displayed image (e.g. invert periodically all or parts of the displayed image). Such a blank displaying will always be noticed by the operator or user.

According to an embodiment, a communication between the observer 121 and the displaying device 51, 61 may be enabled. In such a case, the checking sub-process 10_3, the checker 11_3 and/or the observer 121 can request information that should be embedded into the (invisible) information or security pattern(s) 31. This allows detecting screen casts where someone has recorded a video of the software. Further, also a communication between the updating sub-process 10_2, the updater 11_2 and the checking sub-process 10_3, the checker 11_3 may be enabled. This may be implemented, for example, by use of a corresponding channel, which should be not disturbed. This communication can be used to tell the checking sub-process 10_3 and/or the checker 11_3 about special situations and what it should do in the special situations.

According to a further embodiment, both of the above-mentioned communications may be used to measure time, used for showing information indicating a negative result of the checking. Within this scope, threshold values for the measured time may be utilized, exceeding of which may cause performing of further (more restrictive) possible reactions with regard to the negative result of the checking (e.g., restarting or ending the displaying).

As regards the implementation of (invisible) information or security pattern(s) 31, for example, watermarks known to the skilled person may be used. The watermarks have different positive properties (also known), particularly, robustness to image manipulation. The almost worst image manipulation happens when a recording device 62 like a camera is monitoring the displayed image 13, 612. In this case, the watermark should be so robust that it survives heavy scaling, rotation and noise. When watermarks are used, it can be expected that they will be visible. In that case barcodes may be used as (visible) information or security pattern(s) 31.

If watermarks are used and it is desired that they are invisible when displaying the secured image 13, their invisibility may be achieved by embedding or coding them into the last significant bits of the image parts 321 of the source image 32. The watermarks in the generated secured image parts 131 may become fragile to transformations; however, they will be almost invisible.

For a typical environment of displaying, however, it can be expected that the secured image 13 to be displayed will not be modified (rotated, scaled etc.) during displaying, but that the exact position of the corresponding displaying window may be unknown and/or that the corresponding displaying window displaying the secured image 13 may be at least partly covered by other displaying windows.

A displaying device 51, 61 may display several displaying windows at once, each displaying its own image 13, 612. In this case, all or at least one (a plurality) of the displayed images 13, 612 may be monitored by the observer 121 or the monitoring process 10 respectively.

Further, according to an embodiment, if watermarks are used, they may be utilized as communication channels from the displaying device 51, 61 to the observer 121 and/or the monitoring process 10, which may indicate the observer 121 and/or the monitoring process 10, which information in the displayed image 13, 612 is expected to be visible.

Moreover, according to an embodiment, a system that utilizes tested (and certified) software and/or hardware may contain a signature. If the signature cannot be verified after booting, the system has not been certified. However, it may be required to allow the software and/or hardware to run due to legal reasons (e.g. license terms). Nonetheless, one may not like to assume the liability as the software and/or hardware was not tested or certified respectively. During the boot of the software, the hardware can be reset to a state where the user is informed about that, e.g., by manipulating the displayed image 13, 612. As the hardware means potentially may be limited, a red bar can be generated in the middle of the displayed image 13, 612 or no image 13, 612 may be shown. A certified software and/or hardware that are operated in such a compromised system can deactivate that feature (i.e. remove that red bar) by displaying the "real" information and signaling this to the hardware (observer 121) using watermarking. However, that leads to the question: what is certified software and/or hardware on a compromised system? This is irrelevant, if the watermark(s) needs to be visible, wherein for this requirement they are coded in the most significant bits. Using a suitable definition, it can itself form a known status display that the user recognizes (e.g. a red bar with text that is rendered with pixels so that they form a specific CRC). According to the embodiment, the hardware or observer 121 may comprise or utilize the following: a register, which can be changed only during the boot in order to prevent leaving that mode otherwise; a scanner or detector for scanning the image or video data; a manipulator configured to manipulate the image or video data (e.g. turn it off); and a logic that decides based on the contents of the register and the displayed information, if the image or video data is displayed unchanged (or not).

Summarizing, for supporting correct and reliable operating displaying image data, wherein the image data may change over the time, the present invention suggests a reliable process, by use of which a secured image is generated based on a source image by generating at least one secured image part, wherein the secured image part is generated by combining a source image part of the source image with a corresponding secure pattern; and/or by monitoring displaying the secured image by detecting the corresponding secure pattern of the secured image part and by performing at least one of following: updating the detected secure pattern, checking the currentness or correctness of the detected secure pattern.

It is obvious that the above-described embodiments can be combined in various ways. By means of the above described supporting correct and reliable operating displaying image data a reliable, timely, continuous, effective, fast and resource saving ensuring that an image, which may change over time, is always displayed correctly. Moreover, a reliable operating of displaying image data is enabled also when the displayed image comprises not only changing parts but also parts, which originate from several (reliable and/or unreliable, known and/or unknown) sources.

The invention claimed is:

1. A medical monitoring system for assuring that displayed vital signs of a patient are current, wherein the vital signs may change over time, the medical monitoring system comprising:
   an image generating device, comprising a secured image generator configured to:
      generate a series of secured vital sign image frames by generating at least one secured image part of each vital sign image frame, wherein the secured image part is generated by combining a part of each of a plurality of source vital sign image frames with a corresponding secure pattern to generate the secured vital sign image frames;
   a buffer memory configured to store each of the secure vital sign frames of the series;
   a display device configured to display the series of secured vital sign image frames; and
   a monitoring device configured to monitor displaying each secured vital sign image frame by:
      detecting the corresponding secure pattern in the secured image part of the vital sign image frame currently stored in the buffer memory;
      updating the detected secure pattern by changing data in the secured pattern;
      checking a currentness of the detected secure pattern by checking whether the detected secured pattern corresponds to a last updated secured pattern;
      in response to the detected secure pattern corresponding to the last updated secure pattern, controlling the display device to display the secured vital sign image frame in the buffer memory; and
      in response to determining that the secured vital sign image frame from the buffer memory does not have the last updated secure pattern, controlling the display to one of generate an alert and blank the display screen.

2. The medical monitoring system according to claim 1, wherein the image generating device is configured to generate the secured vital sign image frame by dividing the source vital sign image frame into a plurality of source vital sign image frame parts and by adding the corresponding secure pattern to at least one of the divided source vital sign image frame parts.

3. The medical monitoring system according to claim 1, wherein the secure pattern includes:
   the information allowing identification of currentness of the secured vital sign image frame part including at least one of time information and a sequence counter.

4. The medical monitoring system according to claim 1, wherein the image generating device is configured to generate the secured vital sign image frame by encoding the corresponding secure pattern in at least one of least significant bits of the source vital sign image frame part and encoding the corresponding secure pattern in at least one of most significant bits of the source vital sign image frame part.

5. The medical monitoring system according to claim 1, wherein the image generating device redundantly encodes the corresponding secure pattern.

6. The medical monitoring system according to claim 1, wherein the monitoring device is configured to detect the corresponding secure pattern by scanning at least one preselected row, at least one preselected column, and/or at least one preselected tile of the secured vital sign image frame for an information indicating a possible presence of the secure pattern.

7. The medical monitoring system according to claim 1, wherein controlling the display device to display an alert includes at least one of: indicating that the secured vital sign image frame is not a current secured image, exiting the displaying of the secured vital sign image frame, and restarting the displaying of the secured vital sign image frame.

8. The medical monitoring system according to claim 1, wherein controlling the display device to display an alert includes exiting the displaying of the secured vital sign image frame.

9. The device according to claim 1, wherein the monitoring device is configured to check the currentness of the detected secure pattern at a certain point of time; and/or
after transmitting a request for providing the secured vital sign image frame as currently displayed and receiving the secured vital sign image frame as currently displayed.

10. A method for assuring that displayed vital signs of a patient are current, the method comprising:
generating a series of secured vital sign image frames by generating at least one secured image part of each vital sign frame including combining a part of each of a plurality of source vital sign image frames with a corresponding secure pattern to generate the secured vital sign image frames;
serially storing the secured vital sign image frames in a buffer memory;
displaying a secured vital sign image frame from the buffer memory on a display device;
detecting a corresponding secure pattern in the secured image part of the vital sign image frame stored in the buffer memory and updating the detected secure pattern by changing data in the secure pattern;
checking a currentness of the detected secure pattern by checking whether the detected secure pattern corresponds to a last updated secure pattern;
in response to the detected secure pattern corresponding to the last updated secure pattern, controlling a display device to displayed the secured vital sign image frame from the buffer memory; and
in response to determining that the secured vital sign image frame from the buffer memory does not have the latest updated secure pattern, at least one of blanking the display or displaying an alert.

11. A medical monitoring system for assuring that displayed vital signs of a patient are current, the system comprising:
a frame buffer configured to receive vital sign image frames of a video stream, the image frames each including a depiction of current vital signs of a patient and a secure pattern;
a display device configured to display serially the vital sign image frames of the video stream received from the frame buffer;
a software control device configured to:
i) detect the secure pattern in each vital sign image frame received in the frame buffer,
ii) update the received secure patterns during the display of each of the vital sign image frame,
iii) check the secured pattern to determine whether the vital sign image frame with a most recently updated secure pattern is being displayed, and
iv) in response to determining that the displayed vital sign image frame does not have the most recently updated secure pattern, controlling a display device to at least one of blank the display or issue an alert.

* * * * *